(12) United States Patent
Shiraki

(10) Patent No.: US 11,593,692 B2
(45) Date of Patent: Feb. 28, 2023

(54) GRAPH STRUCTURE ANALYSIS APPARATUS, GRAPH STRUCTURE ANALYSIS METHOD, AND COMPUTER-READABLE RECORDING MEDIUM

(71) Applicant: NEC CORPORATION, Tokyo (JP)

(72) Inventor: Takashi Shiraki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 588 days.

(21) Appl. No.: 16/624,686

(22) PCT Filed: Jun. 19, 2018

(86) PCT No.: PCT/JP2018/023368
§ 371 (c)(1),
(2) Date: Dec. 19, 2019

(87) PCT Pub. No.: WO2018/235841
PCT Pub. Date: Dec. 27, 2018

(65) Prior Publication Data
US 2021/0158194 A1 May 27, 2021

(30) Foreign Application Priority Data
Jun. 20, 2017 (JP) .............................. JP2017-120835

(51) Int. Cl.
*G06N 7/00* (2006.01)
*G06N 3/08* (2006.01)
*G06K 9/62* (2022.01)

(52) U.S. Cl.
CPC ........... *G06N 7/005* (2013.01); *G06K 9/6218* (2013.01); *G06K 9/6232* (2013.01); *G06N 3/08* (2013.01)

(58) Field of Classification Search
USPC ........ 382/155, 159, 190, 218, 225; 703/1–2; 706/46, 48
See application file for complete search history.

(56) References Cited

U.S. PATENT DOCUMENTS

| 7,970,721 | B2 * | 6/2011 | Leskovec | G06F 16/951 |
| | | | | 706/46 |
| 9,270,518 | B2 * | 2/2016 | Muro | G06Q 10/06 |
| 9,715,495 | B1 * | 7/2017 | Tacchi | G06F 40/30 |

(Continued)

FOREIGN PATENT DOCUMENTS

JP 2017-26482 A 2/2017

OTHER PUBLICATIONS

Cho et al., Progressive Graph Matching: Making a Move of Graphs via Probabilistic Voting, 2012 IEEE 978-1-4673-1228-8/12, pp. 398-405. (Year: 2012).*

(Continued)

*Primary Examiner* — Ishrat I Sherali
(74) *Attorney, Agent, or Firm* — Sughrue Mion, PLLC

(57) ABSTRACT

A graph structure analysis apparatus 10 is an apparatus for analyzing a graph structure. The graph structure analysis apparatus 10 includes a range selection unit 11 that selects an analysis target range in the graph structure and a comparison target range to be compared with the analysis target range, and a feature representation extraction unit 12 that extracts a feature representation from data related to the analysis target range and the comparison target range, for each of the ranges.

16 Claims, 16 Drawing Sheets

(56) References Cited

U.S. PATENT DOCUMENTS

| | | | |
|---|---|---|---|
| 9,740,368 B1 * | 8/2017 | Love | G06F 3/04817 |
| 9,787,705 B1 * | 10/2017 | Love | G06F 16/9024 |
| 2004/0199484 A1 * | 10/2004 | Smith | G06F 16/9027 |
| | | | 706/46 |
| 2011/0153601 A1 * | 6/2011 | Nakazawa | G06F 16/3347 |
| | | | 707/723 |

OTHER PUBLICATIONS

Landesberger et al., Visual Analysis of Graphs with Multiple Connected Components, 2009 IEEE 978-1-4244-5283-5/09, pp. 155-162. (Year: 2009).*

Pawar et al., Graph Based K-Nearest Neighbor Minutiae Clustering for Fingerprint Recognition, 2014 IEEE 978-1-4799-5151-2/14, pp. 675-679. (Year: 2014).*

Written Opinion dated Sep. 18, 2018 from the International Searching Authority in International Application No. PCT/JP2018/023368.

Ryohei Fujimaki, et al., "Factorized Asymptotic Bayesian Inference for Mixture Modeling", JMLR W&CP 22, 2012, pp. 400-408.

Riki Eto, et al., "Fully-Automatic Bayesian Piecewise Sparse Linear Models", AISTATS, 2014, pp. 238-246.

F. Rosenblatt, "The Perceptron: A probabilistic model for information storage and organization in the brain", Psychological Review, 1958, pp. 386-408, vol. 65, No. 6.

International Search Report for PCT/JP2018/023368 dated Sep. 18, 2018 [PCT/ISA/210].

* cited by examiner

Fig.4

| FEATURE REPRESENTATION OF (A^B) | SCORE |
|---|---|
| HOT | 10.0 |
| ICE | 8.5 |
| TYPHOON | 3.5 |
| SETTING SUN | 3.0 |
| ... | ... |

Fig.5

| FEATURE REPRESENTATION OF (A^¬B) | SCORE |
|---|---|
| COLD | 7.8 |
| ODEN (JAPANESE WINTER HOT-POT DISH) | 6.6 |
| WIND | 5.9 |
| CONFUSION | 2.1 |
| ... | ... |

GRAPH STRUCTURE ANALYSIS APPARATUS, GRAPH STRUCTURE ANALYSIS METHOD, AND COMPUTER-READABLE RECORDING MEDIUM

CROSS REFERENCE TO RELATED APPLICATIONS

This application is a National Stage of International Application No. PCT/JP2018/023368, filed on Jun. 19, 2018, which claims priority from Japanese Patent Application No. 2017-120835, filed on Jun. 20, 2017, the contents of all of which are incorporated herein by reference in their entirety.

TECHNICAL FIELD

The present invention relates to a graph structure analysis apparatus and a graph structure analysis method for analyzing a graph structure acquired through machine learning, and further relates to a computer-readable recording medium in which a program for realizing them is recorded.

BACKGROUND ART

Commonly, machine learning is performed by constructing a learning model for performing discrimination, regression analysis, and the like using an analyzer. Heterogeneous mixture learning, a neural network (NN), etc. are known as examples of such an analyzer.

Of these, in heterogeneous mixture learning, a decision tree that has a tree structure is constructed as a learning model (for example, see Non-Patent Documents 1 and 2). In addition, in a decision tree constructed through heterogeneous mixture learning, discriminant criteria are set for branches of nodes that are higher than terminal nodes, and a discriminant equation or a regression equation is output from (each of) the terminal nodes. Also, in heterogeneous mixed learning, such discriminant criteria represent the entire learning model, and clarifying the discriminant criteria improves the interpretability of the learning model.

In addition, a neural network (for example, see Non-Patent Document 3) is an analyzer whose practicability has rapidly increased through deep learning and the like. In a neural network, a network structure constituted by multiple layers is constructed by training a model using a large amount of data. Discrimination is then performed at the lowermost end of the network structure.

LIST OF RELATED ART DOCUMENTS

Non-Patent Document

Non-Patent document 1: Ryohei Fujimaki, Satoshi Morinaga, "Factorized Asymptotic Bayesian Inference for Mixture Modeling", JMLR W&CP 22, p. 400-408, 2012

Non-Patent document 2: Riki Eto, et al, "Fully-Automatic Bayesian Piecewise Sparse Linear Models", AISTATS 2014

Non-Patent document 3: Rosenblatt F, "The Perceptron: A probabilistic model for information storage and organization in the brain", Psychological Review, 65, p. 386-408, 1958

SUMMARY OF INVENTION

Problems to be Solved by the Invention

Incidentally, a discriminant criterion selected based on a feature amount set in advance at a branch point is clearly indicated along with a discriminant equation or a regression equation to a user that uses a decision tree constructed through heterogeneous mixture learning. However, normally, data sorted at the branch point is not analyzed to extract a further feature amount from a range that includes feature amounts that have not been set in advance.

In addition, also in a neural network, discrimination that is performed in an intermediate layer called a "hidden layer" between input and output is not made clear to the user, and discrimination processing in an intermediate layer has been a black box.

Therefore, there is a demand for users who use machine learning to be able to evaluate the content of a learning model.

An example object of the invention is to provide a graph structure analysis apparatus, a graph structure analysis method, and a computer-readable recording medium that can solve the above-described problem and enable evaluation of a learning model acquired through machine learning.

Means for Solving the Problems

In order to achieve the aforementioned object, a graph structure analysis apparatus according to one aspect of the invention is an apparatus for analyzing a graph structure, and includes:

a range selection unit configured to select an analysis target range in the graph structure and a comparison target range to be compared with the analysis target range, and a feature representation extraction unit configured to extract a feature representation from data related to the analysis target range and the comparison target range, for each of the ranges.

Also, in order to achieve the aforementioned object, a graph structure analysis method according to one aspect of the invention is a method for analyzing a graph structure, and includes:

(a) a step of selecting an analysis target range in the graph structure and a comparison target range to be compared with the analysis target range; and (b) a step of extracting a feature representation from data related to the analysis target range and the comparison target range, for each of the ranges.

Furthermore, in order to achieve the aforementioned object, a computer readable recording medium according to one aspect of the invention is a non-transitory computer readable recording medium in which a program for causing a computer to analyze a graph structure is recorded, the program including instructions that cause the computer to carry out:

(a) a step of selecting an analysis target range in the graph structure and a comparison target range to be compared with the analysis target range; and (b) a step of extracting a feature representation from data related to the analysis target range and the comparison target range, for each of the ranges.

Advantageous Effects of the Invention

As described above, according to the invention, it is possible to evaluate a learning model acquired through machine learning.

BRIEF DESCRIPTION OF THE DRAWINGS

FIG. 4 is a diagram illustrating an example of feature representations extracted from an analysis target range, in an example embodiment of the invention.

FIG. 5 is a diagram illustrating an example of feature representations extracted from a comparison target range, in an example embodiment of the invention.

EXAMPLE EMBODIMENT

First Example Embodiment

A graph structure analysis apparatus, a graph structure analysis method, and a program in a first example embodiment of the invention will be described below with reference to FIGS. 1 to 7.

[Apparatus Configuration]

Figure 1:
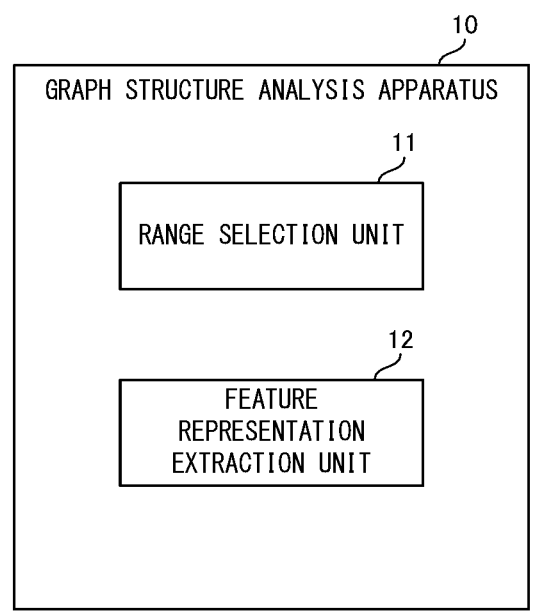
FIG. 1 is a block diagram illustrating a schematic configuration of a graph structure analysis apparatus in a first example embodiment of the invention.

First, a schematic configuration of the graph structure analysis apparatus in the first example embodiment will be described. FIG. 1 is a block diagram illustrating a schematic configuration of the graph structure analysis apparatus in the first example embodiment of the invention.

A graph structure analysis apparatus 10 in this example embodiment shown in FIG. 1 is an apparatus for analyzing a graph structure. As shown in FIG. 1, the graph structure analysis apparatus 10 is provided with a range selection unit 11 and a feature representation extraction unit 12.

The range selection unit 11 selects an analysis target range in a graph structure and a comparison target range to be compared with the analysis target range. The feature representation extraction unit 12 extracts feature representations from data related to the analysis target range and the comparison target range, for each of the ranges.

As described above, in this example embodiment, the graph structure analysis apparatus 10 extracts feature representations for a specific range in the graph structure that constitutes a learning model and a range to be compared with the specific range. Therefore, according to the graph structure analysis apparatus 10, extracted feature representations can be presented, and thus it is possible to evaluate a learning model acquired through machine learning.

Figure 2:
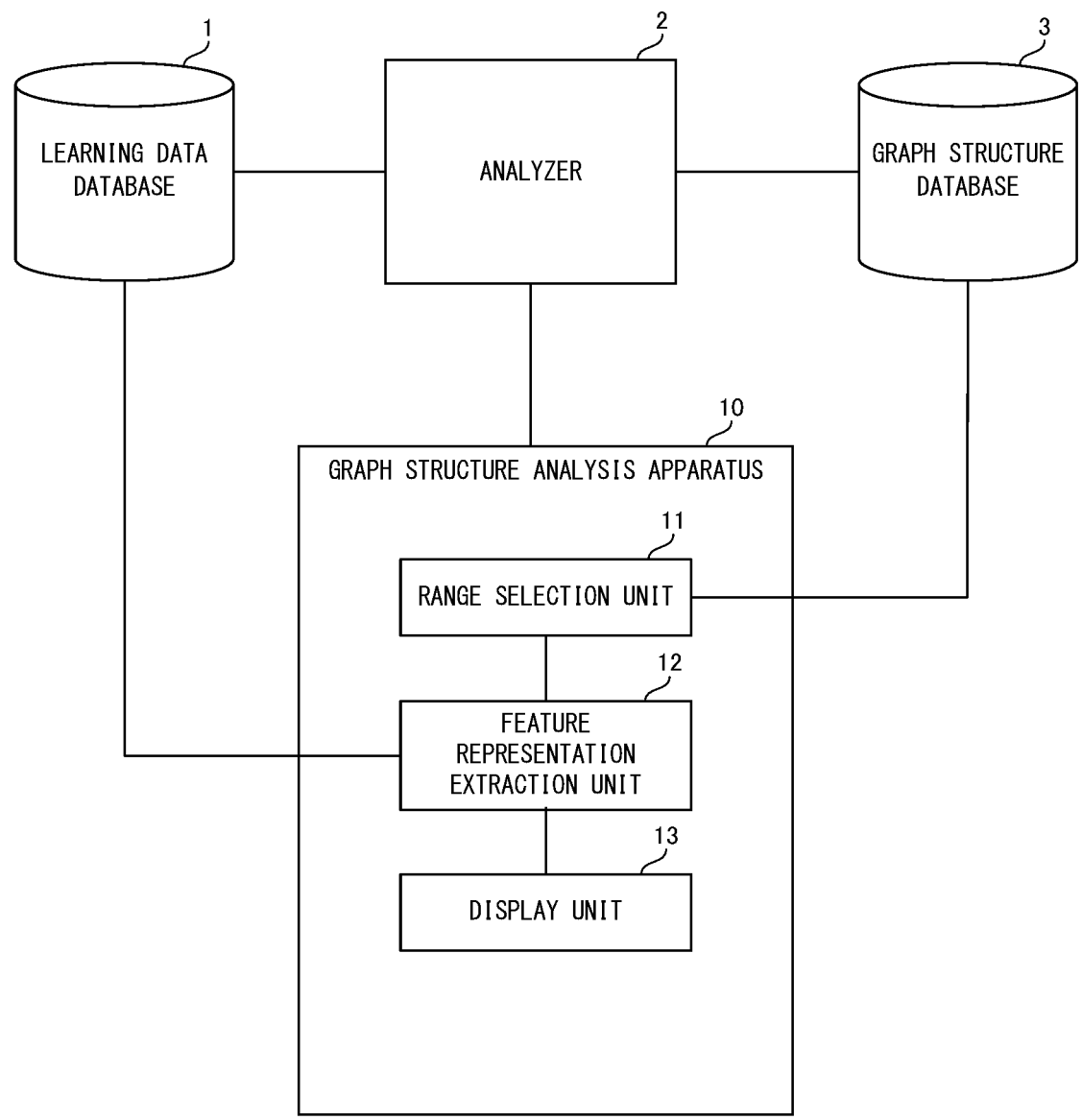
FIG. 2 is a block diagram illustrating a specific configuration of the graph structure analysis apparatus in the first example embodiment of the invention.
Figure 3:
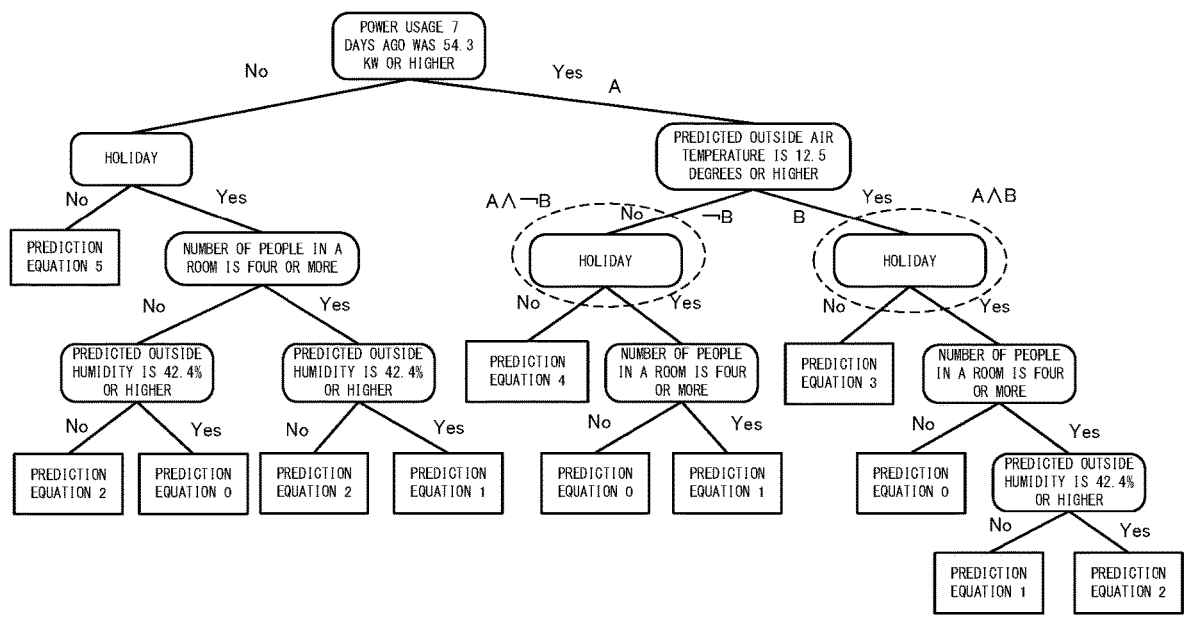
FIG. 3 is a diagram illustrating an example of a graph structure to be analyzed, in an example embodiment of the invention.

Subsequently, a specific configuration of the graph structure analysis apparatus 10 will be described with reference to FIGS. 2 to 5. FIG. 2 is a block diagram illustrating a specific configuration of the graph structure analysis apparatus in the first example embodiment of the invention. FIG. 3 is a diagram illustrating an example of a graph structure to be analyzed in an example embodiment of the invention. FIG. 4 is a diagram illustrating an example of feature representations extracted from an analysis target range, in an example embodiment of the invention. FIG. 5 is a diagram illustrating an example of feature representations extracted from a comparison target range, in an example embodiment of the invention.

As shown in FIG. 2, in the first example embodiment, the graph structure analysis apparatus 10 is connected to a learning data database 1, an analyzer 2, and a graph structure database 3.

The learning data database 1 stores learning data used in machine learning. In addition, the stored learning data is data that has been used in the past or data that is being used at present, in machine learning. Note that the learning data is not limited to time-series data.

The analyzer 2 executes machine learning using learning data stored in the learning data database 1, analyzes numerical data, derives a solution for discrimination, regression, or the like, and generates a graph structure such as a decision tree or a network structure (see FIG. 3) as a learning model. Note that machine learning may be performed using a support vector machine, or may also be performed using a neural network.

The analyzer 2 also stores the generated graph structure in the graph structure database 3. In the example in FIG. 3, the analyzer 2 generates a graph structure for predicting power demand in a building based on past power consumption of the building and environmental information (temperature, humidity, day of the week, number of people in a room, etc.). In addition, in the example in FIG. 3, prediction equations for predicting power demand are stored in the respective terminal nodes of the graph structure.

In addition, in this example embodiment, the graph structure analysis apparatus 10 includes a display unit 13 in addition to the range selection unit 11 and the feature representation extraction unit 12 that have been described above.

In this example embodiment, the range selection unit 11 acquires a graph structure from the graph structure database 3, and selects nodes or a set of nodes for an analysis target range and nodes or a set of nodes for a comparison target range from the nodes that constitute the graph structure. In addition, in this example embodiment, a pair of ranges (an analysis target range and a comparison target range) can be generated for each branch. Furthermore, as will be described in modifications below, such a pair of ranges may be set in a plurality of patterns from one branch.

In this example embodiment, since the graph structure is constructed through machine learning using learning data, the feature representation extraction unit 12 extracts feature representations as data related to the analysis target range and the comparison target range, using learning data stored in the learning data database 1.

Specifically, as shown in FIG. 4, the feature representation extraction unit 12 extracts feature representations of an analysis target range from learning data that passes through the analysis target range, using a x-square test, and provides scores indicating the relationship to the analysis target range, to the extracted feature representations. In addition, as shown in FIG. 5, the feature representation extraction unit 12 extracts feature representations of the comparison target range from learning data that passes through the comparison target range, using the x-square test, and provides scores indicating the relationship to the comparison target range, to the extracted feature representations.

In addition, at this time, the feature representation extraction unit 12 may specify top N feature representations that have high scores, for each of the analysis target range and the comparison target range, and extract the specified N feature representations only. Note that N is any natural number. In addition, the feature representation extraction unit 12 can also acquire knowledge by combining the specified feature representations.

In addition, in this example embodiment, the feature representation extraction unit 12 can also extract feature representations using data other than learning data. Examples of the data other than learning data include text data available to the public on the Internet such as text data in a blog or a microblog. Furthermore, the feature representation extraction unit 12 can also obtain the difference between a feature representation extracted for an analysis target range and a feature representation extracted for a comparison target range.

The display unit 13 displays extracted feature representations for each of the analysis target range and the comparison target range. Specifically, the display unit 13 displays extracted feature representations on the screen of a display apparatus connected to the graph structure analysis apparatus 10 or the screen of a terminal apparatus connected to the graph structure analysis apparatus 10 via a network. In addition, if the feature representation extraction unit 12 obtains the difference between feature representations, the display unit 13 also displays the difference.

[Apparatus Operations]

Figure 6:
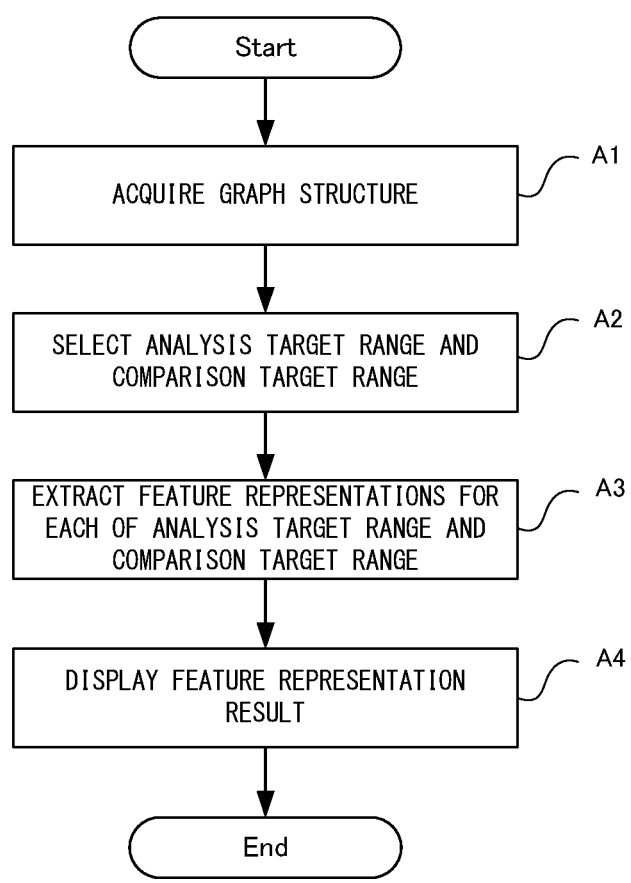
FIG. 6 is a flowchart illustrating operations of the graph structure analysis apparatus in the first example embodiment of the invention.

Next, the graph structure analysis apparatus 10 in the first example embodiment will be described with reference to FIG. 6. FIG. 6 is a flowchart illustrating operations of the graph structure analysis apparatus in the first example embodiment of the invention. The following description will be given with reference to FIGS. 1 to 3 as appropriate. In addition, in the first example embodiment, the graph structure analysis method is carried out by causing the graph structure analysis apparatus to operate. Thus, description of the graph structure analysis method in the first example embodiment is replaced with the following description of operations of the graph structure analysis apparatus 10.

First, assume that the analyzer 2 acquires learning data from the learning data database 1, generates a graph structure as a learning model using the acquired learning data, and stores the generated graph structure in the graph structure database 3. Note that a graph structure may also be output as an intermediate representation depending on the type of the analyzer 2.

As shown in FIG. 4, first, the range selection unit 11 acquires the graph structure from the graph structure database 3 (step A1).

Next, the range selection unit 11 selects an analysis target range from the graph structure and a comparison target range to be compared with the analysis target range (step A2). Note that selection of ranges in step A2 may be performed according to an instruction from the outside, or may also be performed automatically in accordance with a rule that has been set in advance.

Next, the feature representation extraction unit 12 extracts feature representations using data related to the analysis target range and the comparison target range, for each of the ranges (step A3). Specifically, the feature representation extraction unit 12 extracts feature representations of the analysis target range from learning data that passes through the analysis target range and extracts feature representations of the comparison target range from learning data that passes through the comparison target range, using the x-square test.

Next, the display unit 13 displays the extracted feature representations on the screen of the display apparatus or the screen of the terminal apparatus, for each of the analysis target range and the comparison target range (step A4). After step A4 is executed, the processing of the graph structure analysis apparatus ends for the moment.

[Program]

It suffices for the program in the first example embodiment to be a program that causes a computer to execute steps A1 to A4 shown in FIG. 6. By installing this program in a computer and executing the program, it is possible to realize the graph structure analysis apparatus 10 and the graph structure analysis method in this example embodiment. In this case, a CPU (Central Processing Unit) of the computer functions as the range selection unit 11, the feature representation extraction unit 12, and the display unit 13, to perform processing.

In addition, the program in the first example embodiment may also be executed by a computer system constituted by a plurality of computers. In this case, for example, each of the computers may function as one of the range selection unit 11, the feature representation extraction unit 12, and the display unit 13.

Specific Example

Subsequently, a specific example of processing of the graph structure analysis apparatus 10 when the graph structure shown in FIG. 3 is used will be described. First, assume that the learning data database 1 stores environmental information such as past outside air temperature, day of the week, and number of people in a room, as well as time-series data of power consumption of air conditioning, as learning data.

In addition, the analyzer 2 uses such learning data to create a decision tree for distinguishing between ON/OFF of the air conditioner, and derives an equation for predicting power demand using regression equations. Accordingly, the analyzer 2 sets, based on the learning data, regression equations (prediction equations) classified in accordance with the decision tree that has a tree structure. Specifically, the analyzer 2 inputs attribute information such as outside air temperature, day of the week, and number of people in a room, and time series data of power consumption of a specific building, as learning data into an existing machine learning engine, and outputs a graph structure in which regression equations are held at the ends (leaves) as shown in FIG. 3. The graph structure is stored in the graph structure database 3.

The range selection unit 11 selects an analysis target range and a comparison target range to be compared with the analysis target range, in the graph structure shown in FIG. 3. For example, when the second branch on the right "predicted outside air temperature is 12.5 degrees or higher" is focused on, the range selection unit 11 selects "A^B" as an analysis target range, and selects "A^¬B" as a comparison target range. Note that A and B are set as follows.
A: Power usage 7 days ago was 54.3 kW or higher
B: Predicted outside air temperature is 12.5 degrees or higher.

In addition, in this example embodiment, as shown in FIG. 3, A and B may also be set as follows. The range selection unit 11 selects an analysis target range and a comparison target range similarly for the other branches.
A: Power usage 7 days ago was 54.3 kW or higher, and the predicted outside air temperature is 12.5 degrees or higher
B: Day of prediction is a holiday The feature representation extraction unit 12 acquires the analysis target range and the comparison target range from the range selection unit 11, and acquires learning data from the learning data database 1. Feature quantities that are weak in the comparison target range and uniquely intense in the analysis target range are extracted. The feature representation extraction unit 12 then extracts feature representations of the analysis target range (see FIG. 4) from learning data that passes through the analysis target range, and extracts feature representations of the comparison target range (see FIG. 5) from learning data that passes through the comparison target (range), using the x-square test.

In addition, the feature representation extraction unit 12 compares the analysis target range with the comparison target range, and specifies feature representations that are intense only in each of the ranges, for example, feature representations whose score is higher than or equal to a threshold value. Furthermore, the feature representation extraction unit 12 can acquire the following knowledge pieces (1) to (4) based on the specified feature representations. However, the following knowledge pieces acquired here do not necessarily indicate any cause and effect although the knowledge pieces are correlated with each other.
(1) If power usage in the preceding week was high (A), and outside air temperature is high (B), setting sun is related
(2) If outside air temperature is high (B), setting sun is related
(3) If power usage in the preceding week was high (A), and outside air temperature is low (¬B), wind is related
(4) If outside air temperature is low (¬B), wind is related In the above-described example, only "setting sun" and "wind" are extracted as knowledge, but such knowledge can be applied to other words and used as candidates for knowledge. In addition, in the above-described example, all of the feature representations whose score is 1 or higher are adopted. As described above, in this specific example, the graph structure analysis apparatus 10 can analyze a graph structure, and can also provide knowledge candidates that have not existed before.

In addition, in this specific example, the feature representation extraction unit 12 can use data that is different from the learning data used by the analyzer 2. For example, the feature representation extraction unit 12 can also extract feature representations using data different from pieces of environmental information such as outside air temperature, day of the week, and number of people in a room that have been used by the analyzer 2, for example, text data on the Internet such as text data on twitter (registered trademark). Note that, in this case, such data is acquired in a state of being classified according to differences in the outside air temperature, the day of the week, and the number of people in a room, for each time and date when such data was acquired.

Effects of First Example Embodiment

A first effect of the first example embodiment is that, according to the graph structure analysis apparatus 10, feature amounts or knowledge that is not held by the analyzer 2 in advance can be acquired. In addition, the reason why such an effect can be acquired is as follows. In the graph structure analysis apparatus 10, instead of data on terminal nodes, data branched at branch points of the graph structure output by the analyzer 2 is re-learned. Subsequently, in the graph structure analysis apparatus 10, feature representations of two ranges divided at the branch points are extracted through re-learning, and information on classification of the feature amounts at the branch points is also acquired from information other than the information on the branch points.

A second effect of the first example embodiment is that, according to the graph structure analysis apparatus 10, a larger number of more beneficial feature amounts can be acquired. In addition, the reason why such an effect can be obtained is as follows. Branch points of a graph structure are determined to be beneficial and selected by the analyzer 2, unlike learning data itself. Therefore, if data related to the branch points is re-learned, information other than a branch condition can also be acquired. Moreover, the first example embodiment can be applied not only to terminal nodes (leaves) of a graph structure, but also to branches of intermediate layers, and thus feature representations can be extracted more broadly.

A third effect of the first example embodiment is that, according to the graph structure analysis apparatus 10, a logical rule used in abduction performed by the analyzer 2 can be acquired automatically. The reason why such an effect is acquired is as follows. In the graph structure analysis apparatus 10, feature representations of two ranges separated at branch points are extracted through re-learning. In addition, in the graph structure analysis apparatus 10, extracted feature representations can be applied to the relationship between nodes in the graph structure, in other words weights that are set for the respective nodes, and a logical if-then rule set between the nodes, and thus a logical rule can be constructed.

Subsequently, first to fifth modifications in the first example embodiment will be described below.

First Modification

Figure 7:
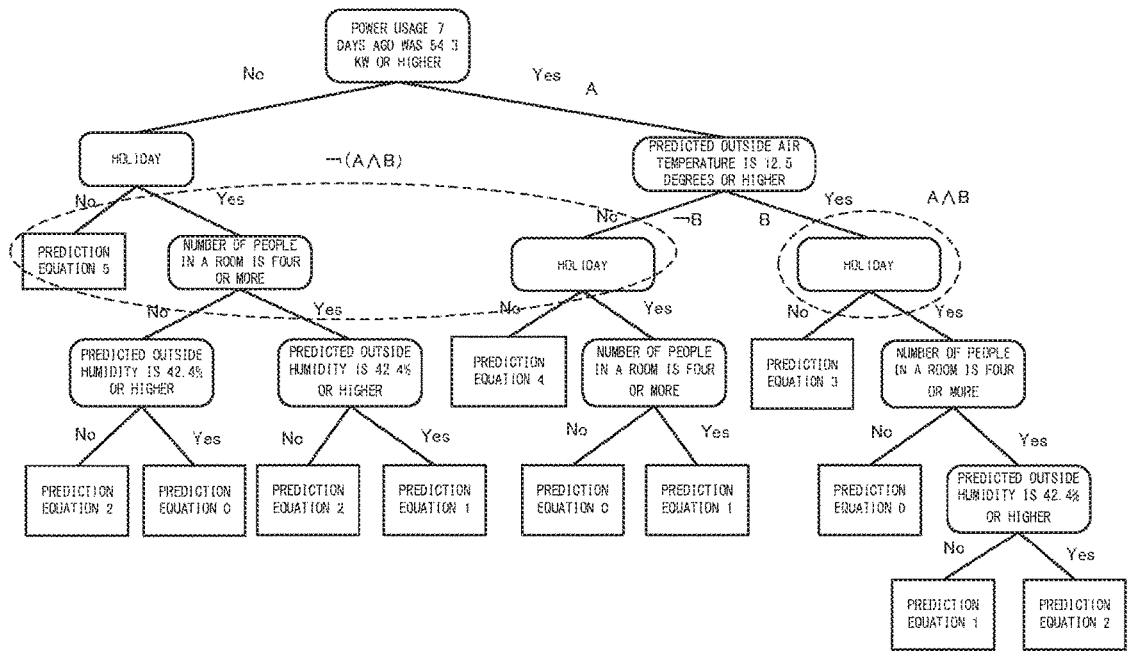
FIGS. 7 (a) and 7 (b) are diagrams illustrating an analysis target range and a comparison target range in a first modification in an example embodiment of the invention, and FIGS. 7 (a) and 7 (b) illustrate different examples.
Figure 7:
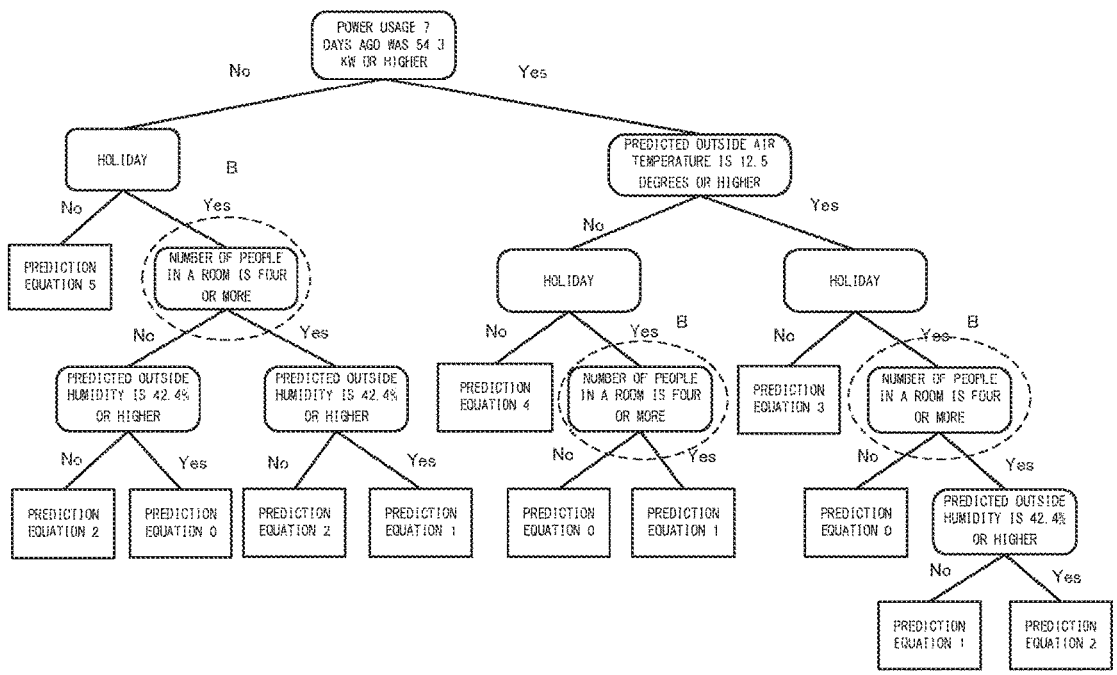

FIGS. 7 (*a*) and 7 (*b*) are diagrams illustrating an analysis target range and a comparison target range in a first modification in an example embodiment of the invention, and FIGS. 7 (a) and 7 (b) show different examples. Graph structures shown in FIGS. 7 (a) and 7 (b) are similar to the graph structure shown in FIG. 3.

In the first modification, unlike the example shown in FIG. 3, the analysis target range may be set to (A^B) and the comparison target range may be set to ¬ (A^B), as shown in FIG. 7 (a). Also, the analysis target range may also be set to B and the comparison target range may also be set to ¬B, as shown in FIG. 7 (b). Note that, in FIG. 7 (a), A and B are similar to those in the above-described specific example, but B in FIG. 7 (b) indicates "holiday".

In this manner, in the first example embodiment, selection of an analysis target range and a comparison target range is not particularly limited. In addition, the number of sets of an analysis target range and a comparison target range that are selected may be one, or two or more.

Second Modification

In a second modification, the feature representation extraction unit 12 performs clustering on related data (learning data or data other than the learning data) to generate a plurality of clusters. The feature representation extraction unit 12 then extracts feature representations from the generated clusters for each of the analysis target range and the comparison target range.

Specifically, the feature representation extraction unit 12 first performs, as preprocessing, clustering on data that passes through A, which is a common portion of the target range (A^B) and the comparison target range (A^¬B). Here, the clustering method may be a k-means method. Next, the feature representation extraction unit 12 extracts feature representations from individual data pieces of each of the clusters acquired through clustering. Examples of a method of extracting feature representations at this time include a $\chi$-square test. Also, a configuration may be adopted in which a score is provided to each representation in accordance with its emergence frequency, and only those with a certain score or higher are extracted as feature representations. Thereafter, the feature representation extraction unit 12 classifies the extracted feature representations into a feature representations belonging to B and a feature representations belonging to ¬B.

According to this second modification, since a feature representation extracted from the common portion is classified into the analysis target range or the comparison target range, a feature representation for which range it belonged to was ambiguous can be clearly classified. In addition, in this second modification, the display unit 13 can display clusters acquired through clustering along with feature representations.

Third Modification

In this third modification, the feature representation extraction unit 12 performs clustering on related data (data that passes through an analysis target range or data for which a comparison target range is to be added) for each of the analysis target range and the comparison target range. Next, the feature representation extraction unit 12 extracts feature representations from each of the acquired clusters. Thereafter, the feature representation extraction unit 12 merges clusters into ranges to which the clusters belong, to classify the feature representations extracted from the respective clusters into the ranges. Note that a method for extracting feature representations is similar to that of the second the modification above. Also, in this third modification, the display unit 13 can display the clusters acquired through clustering along with the feature representations.

Fourth Modification

In the fourth modification, the feature representation extraction unit 12 performs implication clustering on related data (data that passes through an analysis target range or data for which a comparison target range is added) for each of the analysis target range and the comparison target range. When implication clustering is performed, a representative sentence (representative feature representation) that indicates the meaning included in the data of each of the acquired clusters is extracted from the cluster. Therefore, the feature representation extraction unit 12 merges the clusters into the ranges to which the clusters belong, classifies representative sentences extracted from the clusters into the ranges, and sets the classified representative sentences as feature representations of the ranges. Also in this fourth modification, the display unit 13 can display the clusters acquired through clustering along with the feature representations.

Fifth Modification

In this fifth modification, the feature representation extraction unit 12 obtains the difference between a feature representation extracted from an analysis target range and a feature representation extracted from a comparison target range. In addition, the display unit 13 displays the obtained difference on the screen.

Specifically, after extracting a feature representation for each of the analysis target range and the comparison target range, the feature representation extraction unit 12 specifies a feature representation that emerges in common with the analysis target range and the comparison target range. The feature representation extraction unit 12 then merges the score of a feature representation extracted from the analysis target range and the score of the same feature representation extracted from the comparison target range, calculates the difference between the scores, and keeps only the calculated difference as a score.

According to the fifth modification, the score of a feature representation that appears in common with the ranges is diluted, and only the difference is held as a score. Note that, when extracting feature representations by using the above-mentioned x-square test, a common feature representation is not extracted from the ranges, but, when a different technique is used to extract feature representations, there is a possibility that a common feature representation will be extracted. In addition, as described in the first modification, depending on the way an analysis target range and a comparison target range were set, a common feature representation may be extracted from these ranges. Furthermore, also when clustering is performed as in the above second to fourth modifications, a common feature representation may be extracted from the ranges. Furthermore, also in the fourth example embodiment, which will be described later, a common feature representation may be extracted from the ranges.

Second Example Embodiment

Next, a graph structure analysis apparatus, a graph structure analysis method, and a program in a second example embodiment of the invention will be described with reference to FIGS. 8 and 9.

[Apparatus Configuration]

First, a schematic configuration of the graph structure analysis apparatus in the second example embodiment will be described. FIG. 8 is a block diagram illustrating a configuration of the graph structure analysis apparatus in the second example embodiment of the invention.

Figure 8:
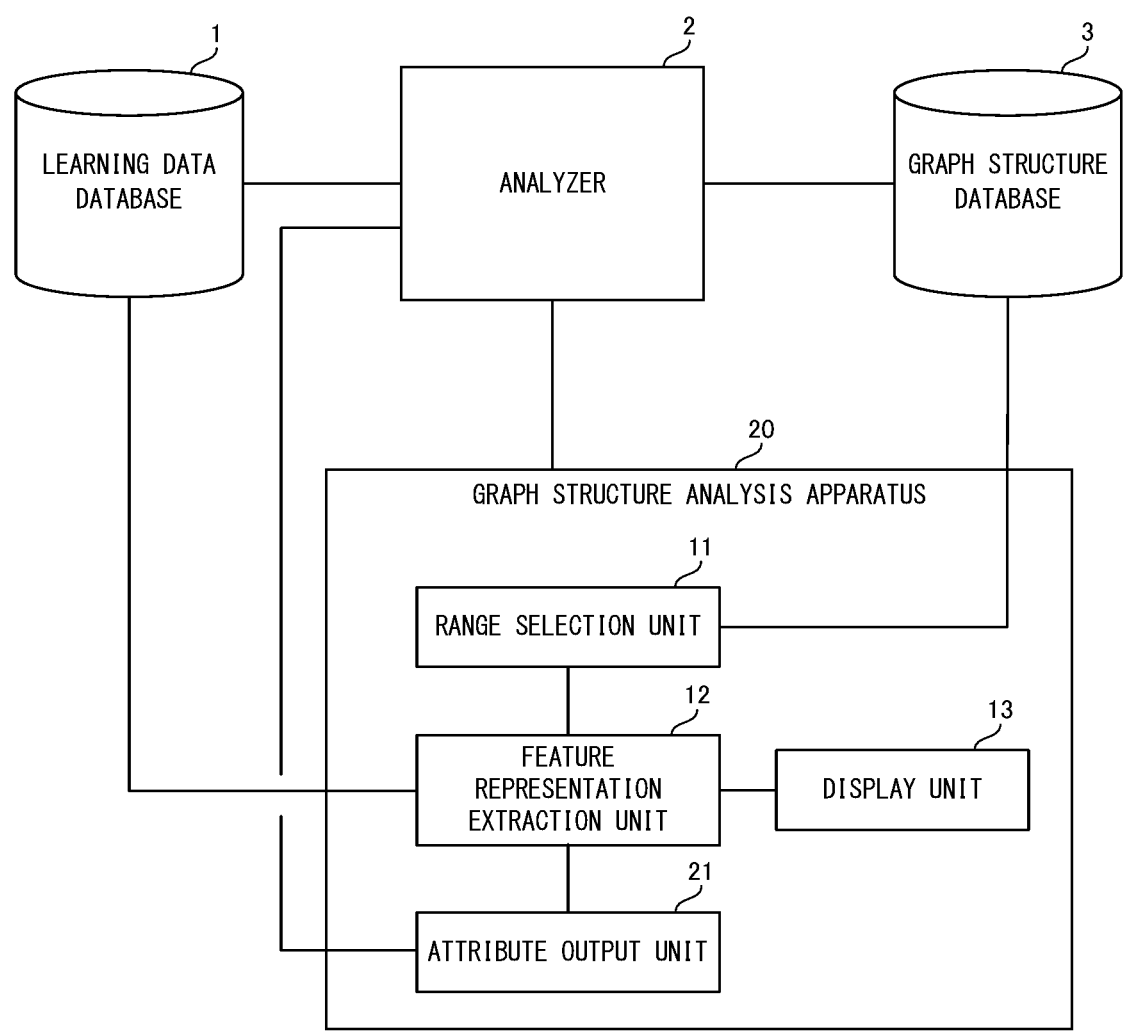
FIG. 8 is a block diagram illustrating a configuration of a graph structure analysis apparatus in a second example embodiment of the invention.

As shown in FIG. 8, a graph structure analysis apparatus 20 in the second example embodiment is provided with an attribute output unit 21, unlike the graph structure analysis apparatus 10 in the first example embodiment shown in FIG. 2. The attribute output unit 21 outputs a feature representation extracted by the feature representation extraction unit 12 as an attribute that is to be used in machine learning, to the analyzer 2. Note that, except for this, the graph structure analysis apparatus 20 is configured in the same manner as the graph structure analysis apparatus 10 in the first example embodiment

[Apparatus Operations]

Next, operations of the graph structure analysis apparatus 20 in this second example embodiment will be described with reference to FIG. 9. FIG. 9 is a flowchart illustrating operations of the graph structure analysis apparatus in the second example embodiment of the invention. The following description will be given with reference to FIG. 8 as appropriate. In addition, in the second example embodiment, the graph structure analysis method is carried out by causing the graph structure analysis apparatus to operate. Thus, description of the graph structure analysis method in the second example embodiment is replaced with the following description of operations of the graph structure analysis apparatus 20.

First, also in the second example embodiment, assume that the analyzer 2 acquires learning data from the learning data database 1, generates a graph structure as a learning model using the acquired learning data, and stores the generated graph structure in the graph structure database 3. Note that there are also cases where the graph structure is output as an intermediate representation depending on the type of the analyzer 2.

Figure 9:
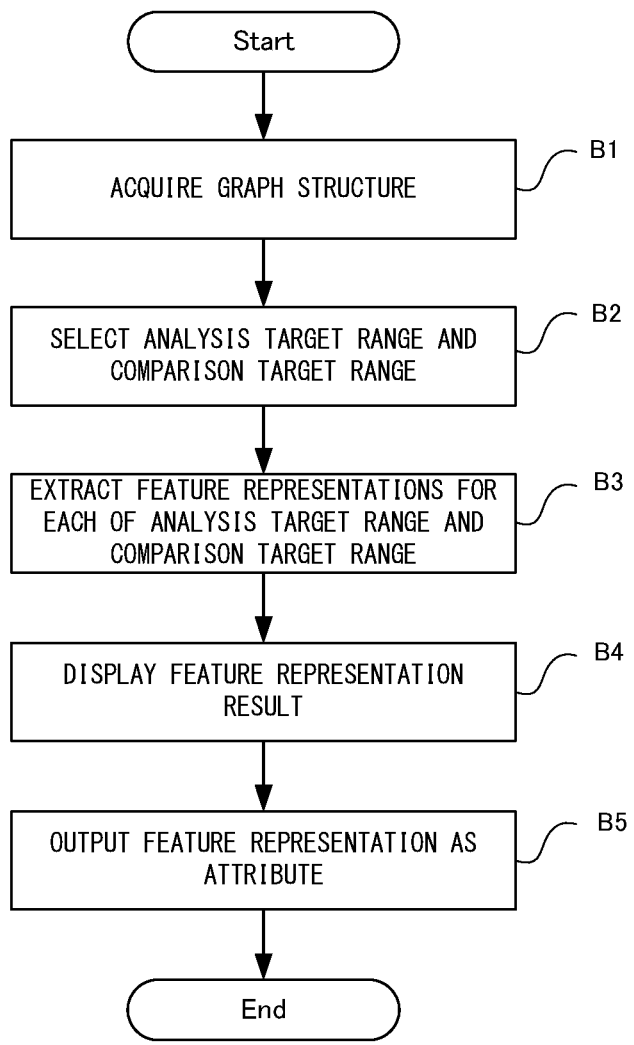
FIG. 9 is a flowchart illustrating operations of the graph structure analysis apparatus in the second example embodiment of the invention.

As shown in FIG. 9, first, the range selection unit 11 executes steps B1 and B2, the feature representation extraction unit 12 then executes step B3, and next, the display unit 13 executes step B4. Steps B1 to B4 are steps respectively similar to steps A1 to A4 shown in FIG. 6.

Next, the attribute output unit 21 outputs a feature representation extracted in step B3, as an attribute to be used in machine learning, to the analyzer 2.

In this manner, in the second example embodiment, the extracted feature representations are added as attributes to be used in machine learning by the analyzer 2. Therefore, in the second example embodiment, if the analyzer 2 re-learns the same learning data, the quality of the graph structure improves.

In existing machine learning represented by the above-mentioned heterogeneous mixture learning, no branch point of a graph structure is newly generated. In machine learning, appropriate branch points are only selected from information prepared in advance and a large number of branch candidates reviewed manually and set manually, and what is not prepared as an option in machine learning is not adopted. Therefore, in existing machine learning, unlike the second example embodiment, an attribute (branch candidate) that needs to be set newly is not acquired, and an effect of feeding back the learning result, in knowledge of abduction, is limited.

[Program]

It suffices for the program in the second example embodiment to be a program that causes a computer to execute steps B1 to B5 shown in FIG. 6. By installing this program in a computer and executing the program, it is possible to realize the graph structure analysis apparatus 10 and the graph structure analysis method in this example embodiment. In this case, a CPU (Central Processing Unit) of the computer functions as the range selection unit 11, the feature representation extraction unit 12, the display unit 13, and the attribute output unit 21, to perform processing.

Moreover, the program in the second example embodiment may also be executed by a computer system constituted by a plurality of computers. In this case, for example, each of the computers may function as one of the range selection unit 11, the feature representation extraction unit 12, the display unit 13, and the attribute output unit 21.

Third Example Embodiment

Next, a graph structure analysis apparatus, a graph structure analysis method, and a program in a third example embodiment of the invention will be described with reference to FIGS. 10 and 11.

[Apparatus Configuration]

First, a schematic configuration of the graph structure analysis apparatus in the third example embodiment will be described. FIG. 10 is a block diagram illustrating a configuration of the graph structure analysis apparatus in the third example embodiment of the invention.

Figure 10:
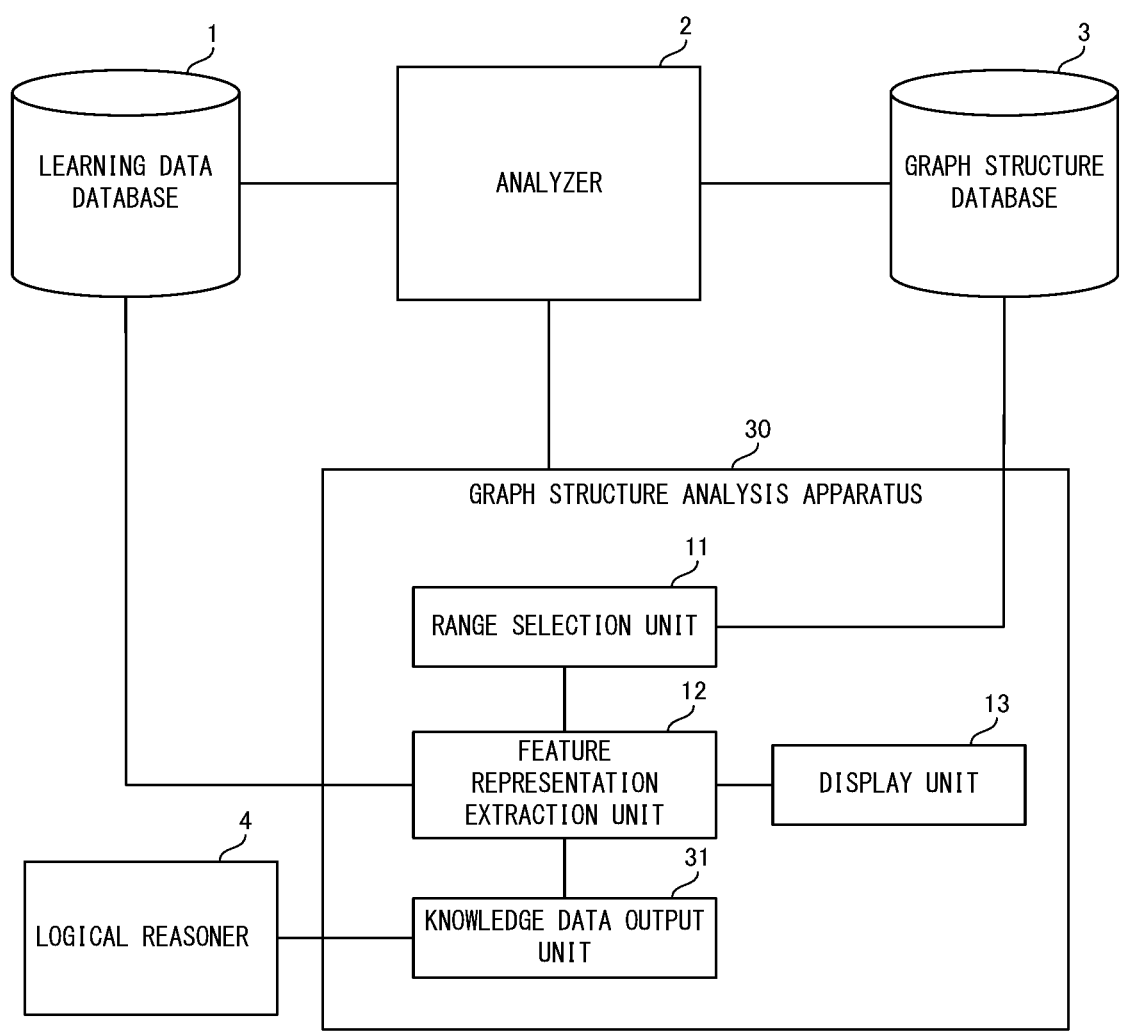
FIG. 10 is a block diagram illustrating a configuration of a graph structure analysis apparatus in a third example embodiment of the invention.

As shown in FIG. 10, a graph structure analysis apparatus 30 in the third example embodiment is connected to a logical reasoner 4 that executes logical reasoning. In addition, in the third example embodiment, the graph structure analysis apparatus 30 is provided with a knowledge data output unit 31, unlike the graph structure analysis apparatus 10 in the first example embodiment illustrated in FIG. 2. The knowledge data output unit 31 outputs feature representations extracted by the feature representation extraction unit 12, as knowledge data to be used in the external logical reasoner 4, to the logical reasoner 4. Note that, except for these, the graph structure analysis apparatus 30 is configured in a similar manner to the graph structure analysis apparatus 10 in the first example embodiment.

[Apparatus Operations]

Next, operations of the graph structure analysis apparatus 30 in the third example embodiment will be described with reference to FIG. 11. FIG. 11 is a flowchart illustrating operations of the graph structure analysis apparatus in the third example embodiment of the invention. The following description will be given with reference to FIG. 10 as appropriate. In addition, in the third example embodiment, the graph structure analysis method is carried out by causing the graph structure analysis apparatus to operate. Thus, description of the graph structure analysis method in the third example embodiment is replaced with the following description of operations of the graph structure analysis apparatus 30.

First, also in the third example embodiment, assume that the analyzer 2 acquires learning data from the learning data database 1, generates a graph structure as a learning model using the acquired learning data, and stores the generated graph structure in the graph structure database 3. Note that there are also cases where a graph structure is output as an intermediate representation depending on the type of the analyzer 2.

Figure 11:
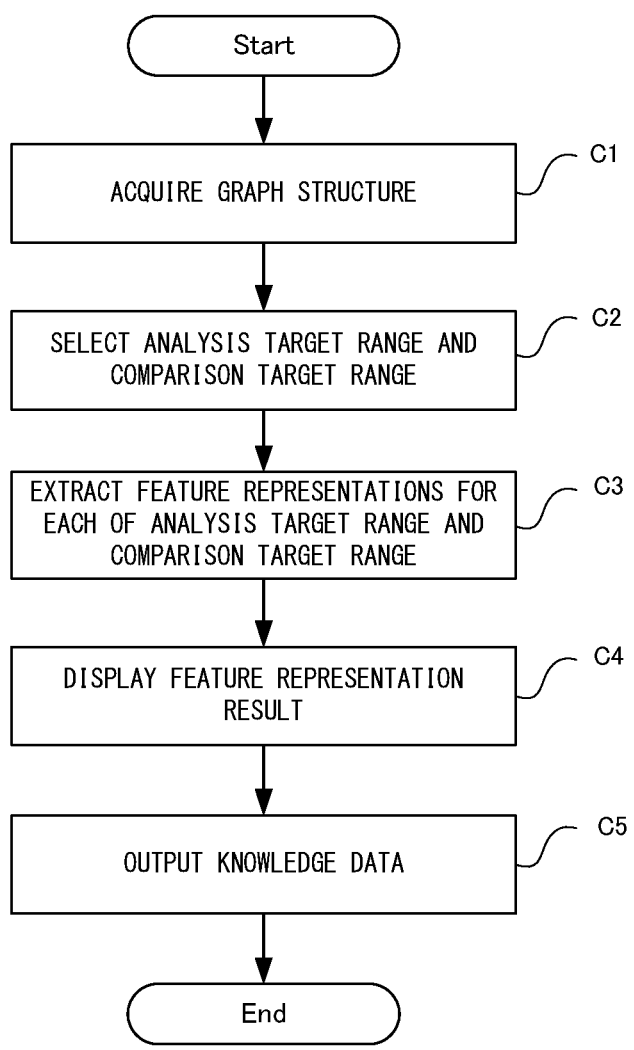
FIG. 11 is a flowchart illustrating operations of the graph structure analysis apparatus in the third example embodiment of the invention.

As shown in FIG. 11, first, the range selection unit 11 executes steps C1 and C2, the feature representation extraction unit 12 then executes step C3, and next, the display unit 13 executes step C4. Steps C1 to C4 are steps respectively similar to steps A1 to A4 shown in FIG. 6.

Next, the knowledge data output unit 31 outputs feature representations extracted by the feature representation extraction unit 12, as knowledge data to be used by the external logical reasoner 4, to a logical reasoner 5 (step C5).

Conventionally, knowledge in abduction has been a very important factor, but has been acquired manually using empirically accumulated know-how and the like. Accordingly, it is very difficult to acquire useful knowledge without involving much labor and cost. In this regard, in the third example embodiment, knowledge used in abduction can be generated automatically.

Fourth Example Embodiment

Next, a graph structure analysis apparatus, a graph structure analysis method, and a program in a fourth example embodiment of the invention will be described with reference to FIGS. 12 and 13.

[Apparatus Configuration]

First, a schematic configuration of the graph structure analysis apparatus in this fourth example embodiment will be described. FIG. 12 is a block diagram illustrating a configuration of the graph structure analysis apparatus in the fourth example embodiment of the invention.

Figure 12:
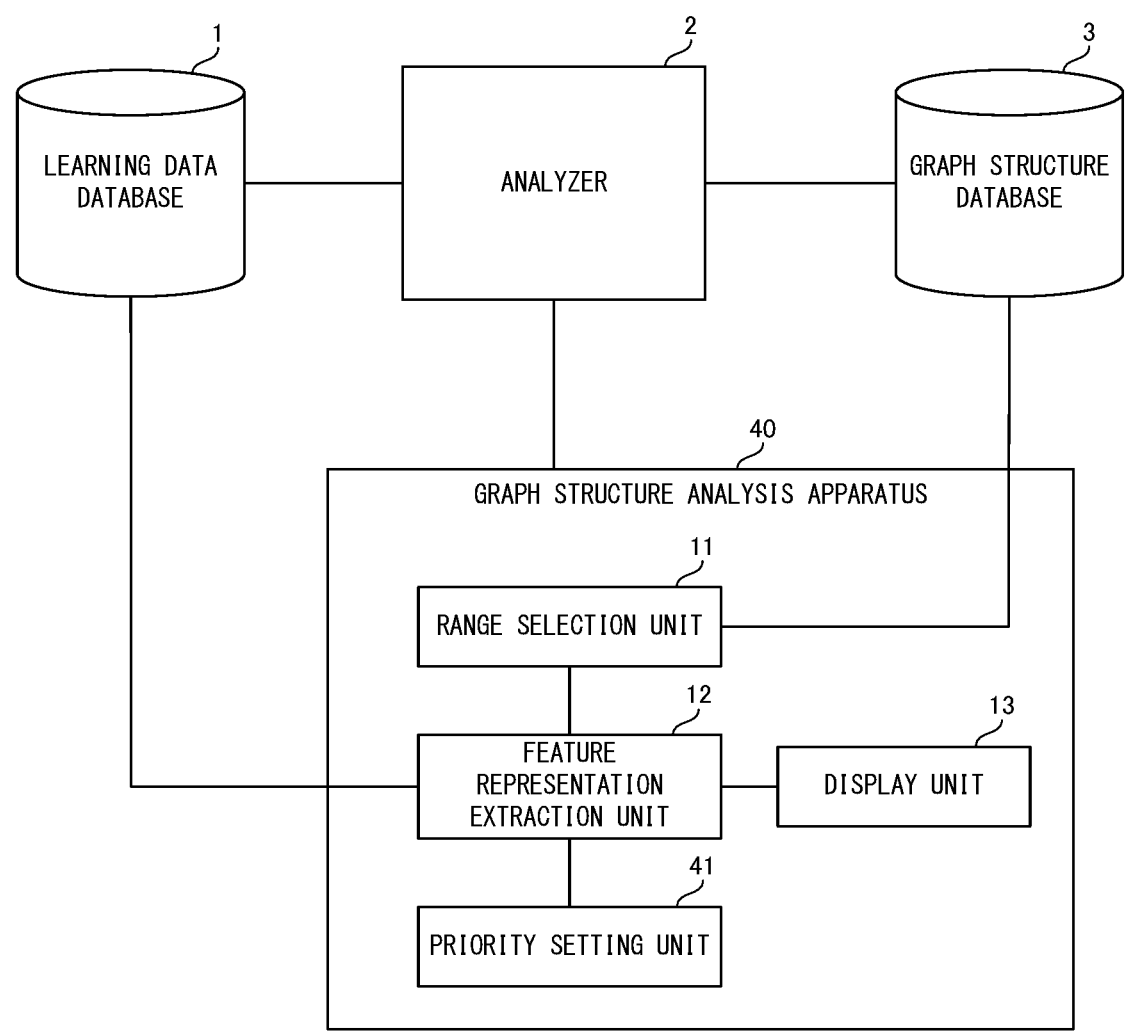
FIG. 12 is a block diagram illustrating a configuration of a graph structure analysis apparatus in a fourth example embodiment of the invention.

As shown in FIG. 12, a graph structure analysis apparatus 40 in this fourth example embodiment is provided with a priority setting unit 41, unlike the graph structure analysis apparatus 10 in the first example embodiment shown in FIG. 2. The priority setting unit 41 sets the priority of feature representations according to the relationship between an analysis target range and a comparison target range. Note that, except for this, the graph structure analysis apparatus 40 is configured in a similar manner to the graph structure analysis apparatus 10 in the first example embodiment.

Specifically, for example, assume that feature representations are extracted from an analysis target range (A^B) and a comparison target range (A^¬B), and feature representations are further extracted from an analysis target range (A'^') and a comparison target range (A'^¬B'). Also, assume that the feature representation extraction unit 12 assigns scores to the extracted feature representations similarly to the first example embodiment.

In this case, the priority setting unit 41 sets the priority of each feature representation by correcting its score according to the stage of the feature representation in the graph structure, for example, according to the distance from a node that is a start point of the range from which the feature representation has been extracted. For example, assuming that, in the graph structure, A is in the first stage and A' is in the second stage, the priority setting unit 41 multiplies the score of a feature representation extracted from the first stage by 1/1, and multiplies the score of a feature representation extracted from the second stage by ½. As a result, the priority of the feature representation extracted from the first stage is higher than the priority of the feature representation extracted from the second stage.

[Apparatus Operations]

Next, operations of the graph structure analysis apparatus 40 in this fourth example embodiment will be described with reference to FIG. 13. FIG. 13 is a flowchart illustrating operations of the graph structure analysis apparatus in the fourth example embodiment of the invention. The following description will be given with reference to FIG. 13 as appropriate. In addition, in this fourth example embodiment, the graph structure analysis method is carried out by operating the graph structure analysis apparatus. Thus, description of the graph structure analysis method in this fourth example embodiment is replaced with the following description of operations of the graph structure analysis apparatus 40.

First, also in this fourth example embodiment, assume that the analyzer 2 acquires learning data from the learning data database 1, generates a graph structure as a learning model using the acquired learning data, and stores the generated graph structure in the graph structure database 3. Note that a graph structure may be output as an intermediate representation depending on the type of the analyzer 2.

Figure 13:
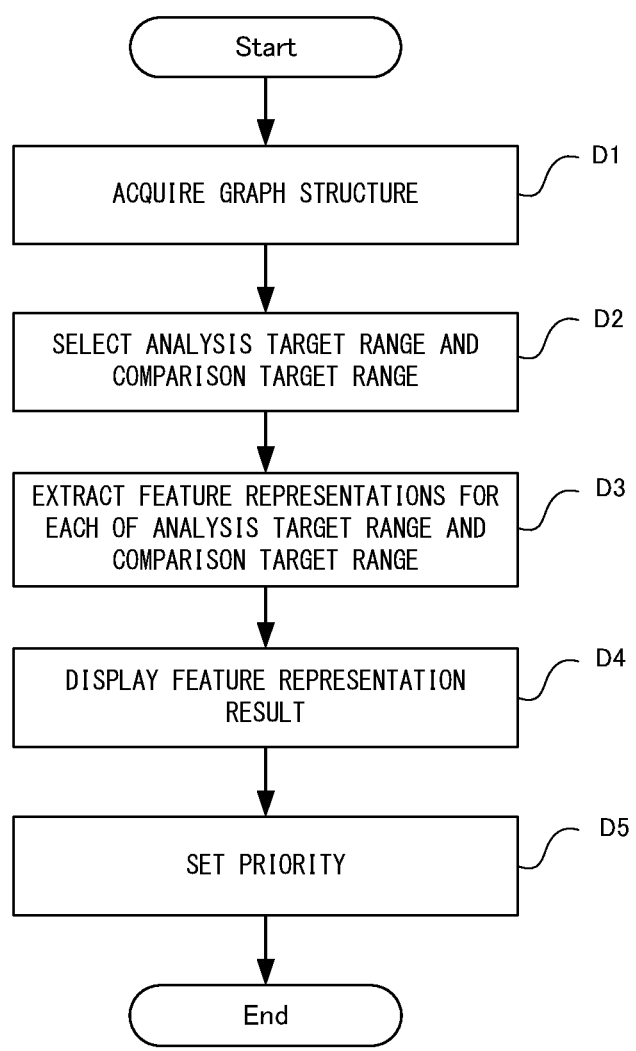
FIG. 13 is a flowchart illustrating operations of the graph structure analysis apparatus in the fourth example embodiment of the invention.

As shown in FIG. 13, first, the range selection unit 11 executes steps D1 and D2, the feature representation extraction unit 12 then executes step D3, and, next, the display unit 13 executes step D4. Steps D1 to D4 are steps respectively similar to steps A1 to A4 shown in FIG. 6.

Next, the priority setting unit 41 sets the priority of feature representations extracted in step D3 according to the relationship between the analysis target range and the comparison target range, specifically according to their stages in the graph structure (step D5).

In this fourth example embodiment, the priority can be set to extracted feature representations in this manner, and thus, when a feature representation is used as an attribute in machine learning, knowledge data in abduction, or the like, the feature representation can be effectively utilized.

Modification a

Figure 14:
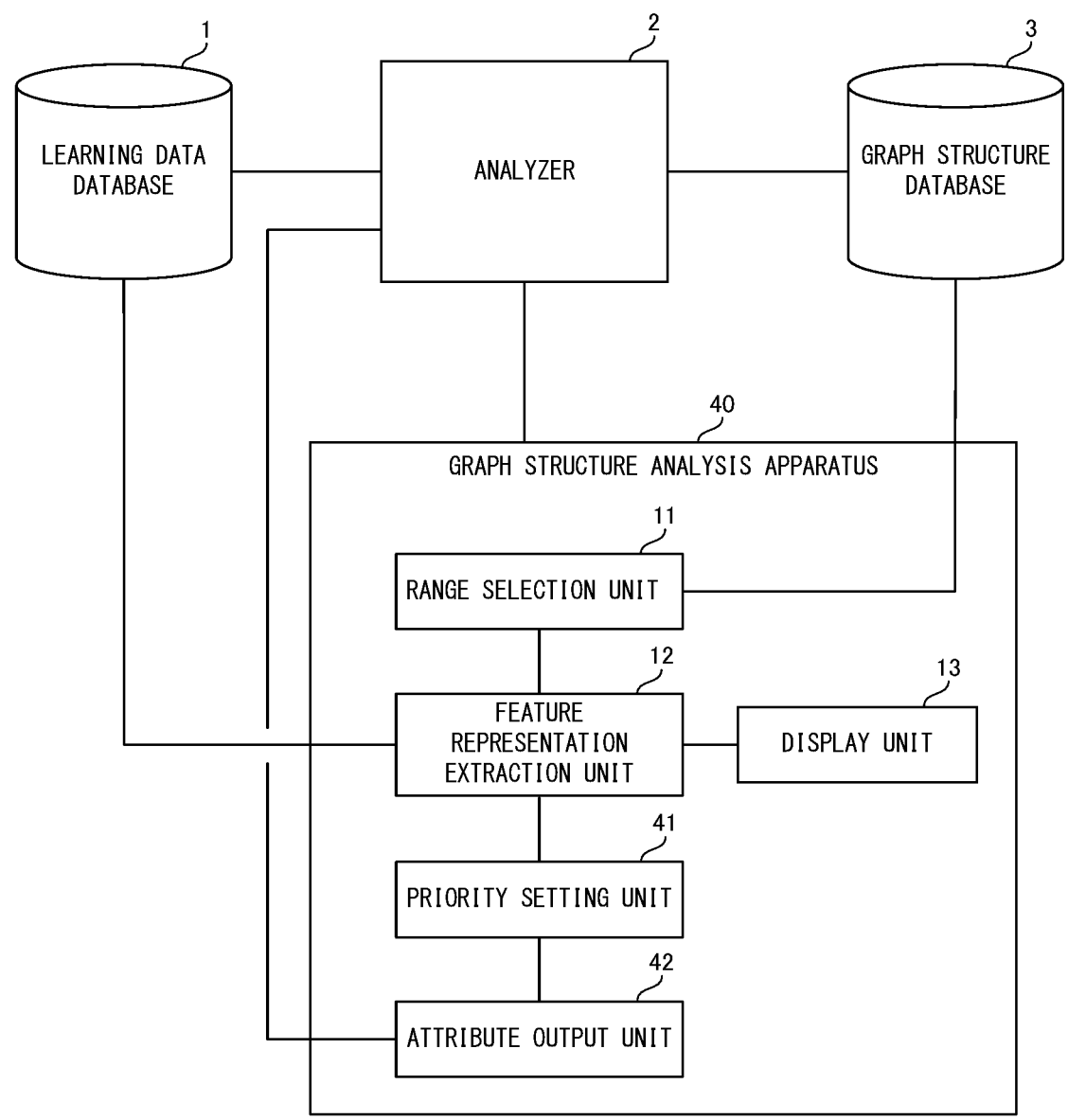
FIG. 14 is a block diagram illustrating a configuration of a modification a of the graph structure analysis apparatus in the fourth example embodiment of the invention.

Subsequently, a modification a in this fourth example embodiment will be described with reference to FIG. 14. FIG. 14 is a block diagram illustrating a configuration of the modification a of the graph structure analysis apparatus in the fourth example embodiment of the invention.

As shown in FIG. 14, in this modification a, unlike the example shown in FIG. 12, an attribute output unit 42 is included. The attribute output unit 42 outputs, to the analyzer 2, only feature representations whose score is higher than or equal to a fixed value from among feature representations extracted by the feature representation extraction unit 12, as attributes to be used in machine learning. In other words, in this modification a, only feature representations whose priority has been increased by the priority setting unit 41 is output to the analyzer 2. Therefore, according to this modification a, the quality of a graph structure can be improved more than in the case of the second example embodiment.

Modification b

Figure 15:
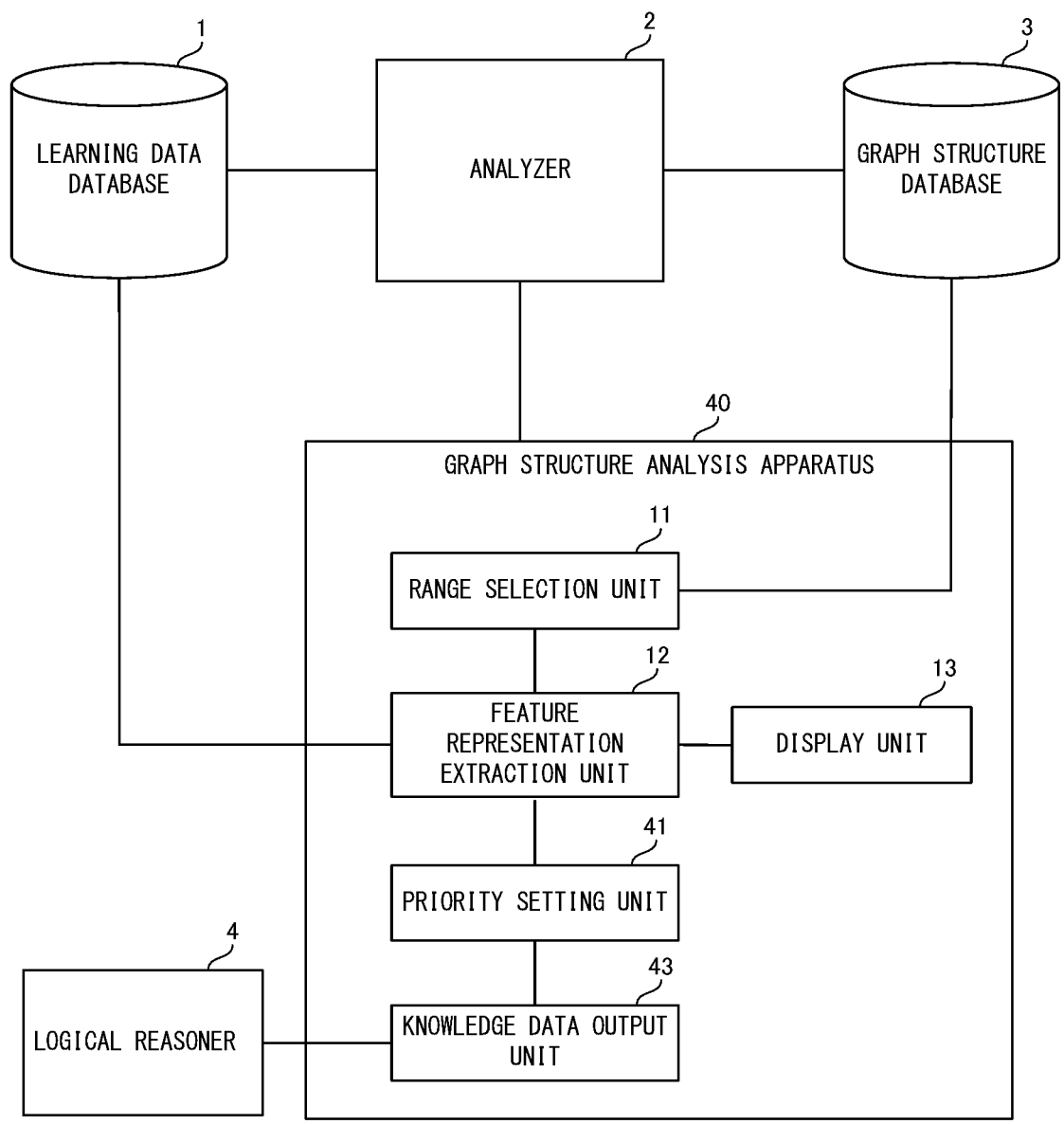
FIG. 15 is a block diagram illustrating a configuration of a modification b of the graph structure analysis apparatus in the fourth example embodiment of the invention.

Subsequently, a modification b in this fourth example embodiment will be described with reference to FIG. 15. FIG. 15 is a block diagram illustrating the configuration of the modification b of the graph structure analysis apparatus in the fourth example embodiment of the invention.

As shown in FIG. 15, in this modification b, unlike the example shown in FIG. 12, a knowledge data output unit 43 is included. The knowledge data output unit 43 outputs, to the logical reasoner 4, only feature representations whose score is higher than or equal to a fixed value from among feature representations extracted by the feature representation extraction unit 12, as knowledge data to be used by the external logical reasoner 4. In other words, in this modification b, only feature representations whose priority has been increased by the priority setting unit 41 is output to the logical reasoner 4. Therefore, according to this modification b, it is possible to generate more appropriate knowledge than in the third example embodiment.

Modification c

In this modification c, the priority setting unit 41 can set the priority of a feature representation in accordance with how an analysis target range and a comparison target range are selected, instead of its stage in a graph structure.

For example, if the analysis target range is (A^B), and the comparison target range is (A^¬B), the priority setting unit 41 sets the score of a feature representation extracted from the comparison target range to be the same as the score of a feature representation extracted from the analysis target range. Also, if the analysis target range is (A^B), and the comparison target range is ¬(A^B), the priority setting unit 41 sets the score of a feature representation extracted from the comparison target range to be twice the score of the feature representation extracted from the analysis target range. Furthermore, if the analysis target range is (B), and the comparison target range is (¬B), the priority setting unit 41 sets the score of a feature representation extracted from the comparison target range to be ½ of the score of the feature representation extracted from the analysis target range.

[Physical Configuration]

Figure 16:
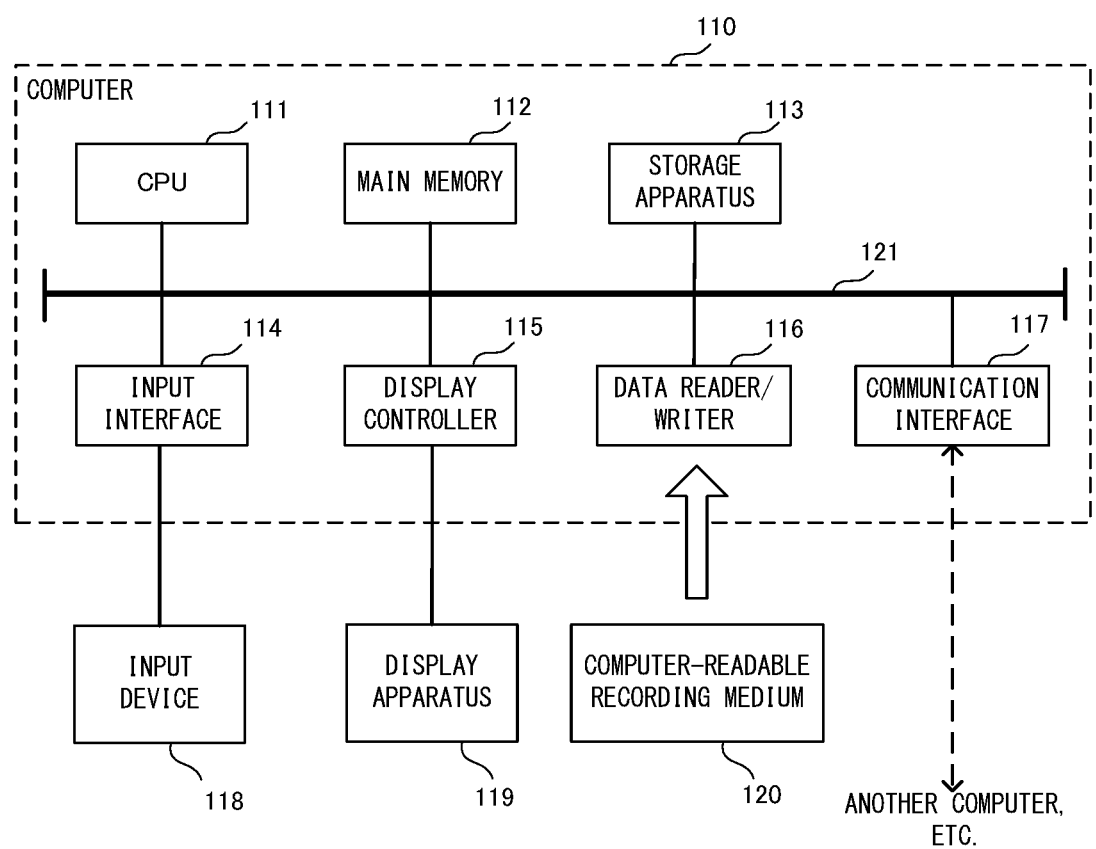
FIG. 16 is a block diagram illustrating an example of a computer for realizing the graph structure analysis apparatus in the first to fourth example embodiments of the invention.

Here, a computer for realizing a graph structure analysis apparatus by executing the program in the first to fourth example embodiments will be described with reference to FIG. 16. FIG. 16 is a block diagram illustrating an example of a computer for realizing the graph structure analysis apparatus in the first to fourth example embodiments of the invention.

As shown in FIG. 16, a computer 110 includes a CPU 111, a main memory 112, a storage apparatus 113, an input interface 114, a display controller 115, a data reader/writer 116, and a communication interface 117. These constituent elements are connected via a bus 121 to enable mutual data communication. Note that the computer 110 may also include a GPU (Graphics Processing Unit) or an FPGA (Field-Programmable Gate Array), in addition to the CPU 111 or in place of the CPU 111.

The CPU 111 carries out various types of calculation by deploying, in the main memory 112, programs (codes) in this example embodiment stored in the storage apparatus 113, and executing codes in a predetermined order. Typically, the main memory 112 is a volatile storage apparatus such as a DRAM (Dynamic Random Access Memory). In addition, the program in this example embodiment is provided in a state of being stored in a computer-readable recording medium 120. Note that the program in this example embodiment may also be distributed on the Internet connected via the communication interface 117.

In addition, specific examples of the storage apparatus 113 include a hard disk drive and a semiconductor storage apparatus such as a flash memory. The input interface 114 mediates data transmission between the CPU 111 and an input device 118 including a keyboard and a mouse. The display controller 115 is connected to a display apparatus 119 to control display on the display apparatus 119.

The data reader/writer 116 mediates data transmission between the CPU 111 and the recording medium 120, reads out a program from the recording medium 120, and writes a processing result of the computer 110 to the recording medium 120. The communication interface 117 mediates data transmission between the CPU 111 and another computer.

Furthermore, specific examples of the recording medium 120 include a general-purpose semiconductor storage device such as a Compact Flash (CF (registered trademark)) and a Secure Digital (SD), a magnetic recording medium such as a flexible disk, or an optical recording medium such as a Compact Disk Read Only Memory (CD-ROM).

Note that the graph structure analysis apparatus 10 in the first to fourth example embodiments can also be realized by using items of hardware corresponding to the units, instead of a computer in which programs are installed. Furthermore, a configuration may also be adopted in which a portion of the graph structure analysis apparatus 10 is realized by a program, and the remaining portion is realized by hardware.

Part of or all of the above-described example embodiments can be expressed in the below-described Supplementary Notes 1 to 30, but the present invention is not limited to the below description.

Supplementary Note 1

A graph structure analysis apparatus for analyzing a graph structure, comprising: a range selection unit configured to select an analysis target range in the graph structure and a comparison target range to be compared with the analysis target range; and a feature representation extraction unit configured to extract a feature representation from data related to the analysis target range and the comparison target range, for each of the ranges.

Supplementary Note 2

The graph structure analysis apparatus according to Supplementary Note 1, further comprising:

a display unit configured to display the extracted feature representation for each of the analysis target range and the comparison target range.

Supplementary Note 3

The graph structure analysis apparatus according to Supplementary Note 2, wherein the feature representation extraction unit performs clustering on the data related to the analysis target range and the comparison target range to generate a plurality of clusters, and extracts the feature representation from the generated clusters for each of the analysis target range and the comparison target range, and the display unit displays the plurality of clusters in addition to the extracted feature representation for each of the analysis target range and the comparison target range.

Supplementary Note 4

The graph structure analysis apparatus according to Supplementary Note 3, wherein the feature representation extraction unit performs implication clustering on the data related to the analysis target range and the comparison target range, for each of the ranges.

Supplementary Note 5

The graph structure analysis apparatus according to any one of Supplementary Notes 2 to 4,
wherein the feature representation extraction unit obtains a difference between a feature representation extracted from the analysis target range and a feature representation extracted from the comparison target range, and
the display unit displays the difference.

Supplementary Note 6

The graph structure analysis apparatus according to any one of Supplementary Notes 1 to 5,
wherein the graph structure is constructed through machine learning using learning data, and
the feature representation extraction unit uses the learning data or data other than the learning data as the data related to the analysis target range and the comparison target range, to extract the feature representation.

Supplementary Note 7

The graph structure analysis apparatus according to Supplementary Note 6, further comprising
a priority setting unit configured to set a priority of the feature representation according to a relationship between the analysis target range and the comparison target range.

Supplementary Note 8

The graph structure analysis apparatus according to Supplementary Note 7,
wherein the priority setting unit sets the priority of the feature representation according to stages of the analysis target range and the comparison target range in the graph structure.

Supplementary Note 9

The graph structure analysis apparatus according to Supplementary Note 6, further comprising
an attribute output unit configured to output the extracted feature representation as an attribute to be used in the machine learning.

Supplementary Note 10

The graph structure analysis apparatus according to any one of Supplementary Notes 1 to 9, further comprising
a knowledge data output unit configured to output the extracted feature representation as knowledge data to be used by an external logical reasoner.

Supplementary Note 11

A graph structure analysis method for analyzing a graph structure, comprising:
(a) a step of selecting an analysis target range in the graph structure and a comparison target range to be compared with the analysis target range; and
(b) a step of extracting a feature representation from data related to the analysis target range and the comparison target range, for each of the ranges.

Supplementary Note 12

The graph structure analysis method according to Supplementary Note 11, further comprising
(c) a step of displaying the extracted feature representation for each of the analysis target range and the comparison target range.

Supplementary Note 13

The graph structure analysis method according to Supplementary Note 12,
wherein, in the (b) step, clustering is performed on the data related to the analysis target range and the comparison target range to generate a plurality of clusters, and the feature representation is extracted from the generated clusters for each of the analysis target range and the comparison target range, and
in the (c) step, the plurality of clusters is displayed in addition to the extracted feature representation for each of the analysis target range and the comparison target range.

Supplementary Note 14

The graph structure analysis method according to Supplementary Note 13,
wherein, in the (b) step, implication clustering is performed on the data related to the analysis target range and the comparison target range, for each of the ranges.

Supplementary Note 15

The graph structure analysis method according to any one of Supplementary Notes 12 to 14,
wherein, in the (b) step, a difference between a feature representation extracted for the analysis target range and a feature representation extracted for the comparison target range is obtained, and
in the (c) step, the difference is displayed.

Supplementary Note 16

The graph structure analysis method according to any one of Supplementary Notes 11 to 15,
wherein the graph structure is constructed through machine learning using learning data, and
in the (b) step, the learning data or data other than the learning data is used as the data related to the analysis target range and the comparison target range, to extract the feature representation.

Supplementary Note 17

The graph structure analysis method according to Supplementary Note 16, further comprising
(d) a step of setting a priority of the feature representation according to a relationship between the analysis target range and the comparison target range.

Supplementary Note 18

The graph structure analysis method according to Supplementary Note 17,
wherein, in the (b) step, the priority is set for the feature representation according to stages of the analysis target range and the comparison target range in the graph structure.

Supplementary Note 19

The graph structure analysis method according to Supplementary Note 16, further comprising
(e) a step of outputting the extracted feature representation as an attribute to be used in the machine learning.

Supplementary Note 20

The graph structure analysis method according to any one of Supplementary Notes 11 to 19, further comprising
(f) a step of outputting the extracted feature representation as knowledge data to be used by an external logical reasoner.

Supplementary Note 21

A computer readable recording medium in which a program for causing a computer to analyze a graph structure is recorded, the program including instructions that cause the computer to carry out:
(a) a step of selecting an analysis target range in the graph structure and a comparison target range to be compared with the analysis target range; and
(b) a step of extracting a feature representation from data related to the analysis target range and the comparison target range, for each of the ranges.

Supplementary Note 22

The computer readable recording medium according to Supplementary Note 21,
wherein the program further includes an instruction that causes the computer to carry out:
(c) a step of displaying the extracted feature representation for each of the analysis target range and the comparison target range.

Supplementary Note 23

The computer readable recording medium according to Supplementary Note 22,
wherein, in the (b) step, clustering is performed on the data related to the analysis target range and the comparison target range to generate a plurality of clusters, and the feature representation is extracted from the generated clusters for each of the analysis target range and the comparison target range, and
in the (c) step, the plurality of clusters is displayed in addition to the extracted feature representation for each of the analysis target range and the comparison target range.

Supplementary Note 24

The computer readable recording medium according to Supplementary Note 23,
wherein, in the (b) step, implication clustering is performed on the data related to the analysis target range and the comparison target range, for each of the ranges.

Supplementary Note 25

The computer readable recording medium according to any one of Supplementary Notes 22 to 24,
wherein, in the (b) step, a difference between a feature representation extracted for the analysis target range and a feature representation extracted for the comparison target range is obtained, and
in the (c) step, the difference is displayed.

Supplementary Note 26

The computer readable recording medium according to any one of Supplementary Notes 21 to 25,
wherein the graph structure is constructed through machine learning using learning data, and
in the (b) step, the learning data or data other than the learning data is used as the data related to the analysis target range and the comparison target range, to extract the feature representation.

Supplementary Note 27

The computer readable recording medium according to Supplementary Note 26,
wherein the program further includes an instruction that causes the computer to carry out:
(d) a step of setting a priority of the feature representation according to a relationship between the analysis target range and the comparison target range.

Supplementary Note 28

The computer readable recording medium according to Supplementary Note 27,
wherein, in the (d) step, the priority is set for the feature representation according to stages of the analysis target range and the comparison target range in the graph structure.

Supplementary Note 29

The computer readable recording medium according to Supplementary Note 26,
wherein the program further includes an instruction that causes the computer to carry out:
(e) a step of outputting the extracted feature representation as an attribute to be used in the machine learning.

Supplementary Note 30

The computer readable recording medium according to any one of Supplementary Notes 21 to 29,
wherein the program further includes an instruction that causes the computer to carry out:
(f) a step of outputting the extracted feature representation as knowledge data to be used by an external logical reasoner.

Although the present invention has been described above with reference to the example embodiments above, the invention is not limited to the above example embodiments. Various modifications understandable to a person skilled in the art can be made to configurations and details of the invention, within the scope of the invention.

INDUSTRIAL APPLICABILITY

As described above, according to the invention, it is possible to evaluate a learning model acquired through machine learning. Thus, the invention is useful when adding rationalizations including large-scale cases that need scalability, for example, in various analysis cases in which an existing analyzer is used, by extracting feature representations based on branches selected by an analyzer. Furthermore, the invention is useful for adding attribute candidates for improving the accuracy of various analysis solutions for which an existing analyzer is used. In addition, the invention is useful for automatically/semi-automatically adding various analysis solutions used in a logical reasoner and knowledge used for decision-making solutions.

LIST OF REFERENCE SIGNS

- 1 Learning data database
- 2 Analyzer
- 3 Graph structure database
- 4 Logical reasoner
- 10 Graph structure analysis apparatus (first example embodiment)
- 11 Range selection unit
- 12 Feature representation extraction unit
- 13 Display unit
- 20 Graph structure analysis apparatus (second example embodiment)
- 21 Attribute output unit
- 30 Graph structure analysis apparatus (third example embodiment)
- 31 Knowledge data output unit
- 40 Graph structure analysis apparatus (fourth example embodiment)
- 41 Priority setting unit
- 110 Computer
- 111 CPU
- 112 Main memory
- 113 Storage apparatus
- 114 Input interface
- 115 Display controller
- 116 Data reader/writer
- 117 Communication interface
- 118 Input device
- 119 Display apparatus
- 120 Recording medium
- 121 Bus

The invention claimed is:

1. A graph structure analysis apparatus for analyzing a graph structure, comprising:
   a processor; and
   a memory storing executable instructions that, when executed by the processor, causes the processor to perform as:
   a range selection unit configured to select an analysis target range in the graph structure and a comparison target range to be compared with the analysis target range;
   a feature representation extraction unit configured to extract a feature representation from data related to the analysis target range and the comparison target range, for each of the ranges; and
   a display unit configured to display the extracted feature representation for each of the analysis target range and the comparison target range,
   wherein the feature representation extraction unit performs clustering on the data related to the analysis target range and the comparison target range to generate a plurality of clusters, and extracts the feature representation from the generated clusters for each of the analysis target range and the comparison target range, and
   the display unit displays the plurality of clusters in addition to the extracted feature representation for each of the analysis target range and the comparison target range.

2. The graph structure analysis apparatus according to claim 1,
   wherein the feature representation extraction unit performs implication clustering on the data related to the analysis target range and the comparison target range, for each of the ranges.

3. The graph structure analysis apparatus according to claim 1,
   wherein the feature representation extraction unit obtains a difference between a feature representation extracted from the analysis target range and a feature representation extracted from the comparison target range, and
   the display unit displays the difference.

4. The graph structure analysis apparatus according to claim 1,
   wherein the graph structure is constructed through machine learning using learning data, and
   the feature representation extraction unit uses the learning data or data other than the learning data as the data related to the analysis target range and the comparison target range, to extract the feature representation.

5. The graph structure analysis apparatus according to claim 4, wherein the processor further performs as:
   a priority setting unit configured to set a priority of the feature representation according to a relationship between the analysis target range and the comparison target range.

6. The graph structure analysis apparatus according to claim 5,
   wherein the priority setting unit sets the priority of the feature representation according to stages of the analysis target range and the comparison target range in the graph structure.

7. The graph structure analysis apparatus according to claim 4, wherein the processor further performs as:
   attribute output unit configured to output the extracted feature representation as an attribute to be used in the machine learning.

8. The graph structure analysis apparatus according to claim 1, wherein the processor further performs as:
   knowledge data output unit configured to output the extracted feature representation as knowledge data to be used by an external logical reasoner.

9. A graph structure analysis method for analyzing a graph structure, comprising:
   selecting an analysis target range in the graph structure and a comparison target range to be compared with the analysis target range;
   extracting a feature representation from data related to the analysis target range and the comparison target range, for each of the ranges;
   displaying the extracted feature representation for each of the analysis target range and the comparison target range,
   wherein, in the extracting, clustering is performed on the data related to the analysis target range and the comparison target range to generate a plurality of clusters, and the feature representation is extracted from the generated clusters for each of the analysis target range and the comparison target range, and
   in the displaying, the plurality of clusters is displayed in addition to the extracted feature representation for each of the analysis target range and the comparison target range.

10. The graph structure analysis method according to claim 9,
   wherein, in the extracting, implication clustering is performed on the data related to the analysis target range and the comparison target range, for each of the ranges.

11. The graph structure analysis method according to claim 9,
   wherein, in the extracting, a difference between a feature representation extracted for the analysis target range and a feature representation extracted for the comparison target range is obtained, and
   in the displaying, the difference is displayed.

12. The graph structure analysis method according to claim 9,
   wherein the graph structure is constructed through machine learning using learning data, and
   in the extracting, the learning data or data other than the learning data is used as the data related to the analysis target range and the comparison target range, to extract the feature representation.

13. The graph structure analysis method according to claim 12, further comprising
   setting a priority of the feature representation according to a relationship between the analysis target range and the comparison target range.

14. The graph structure analysis method according to claim 13,
   wherein, in the extracting, the priority is set for the feature representation according to stages of the analysis target range and the comparison target range in the graph structure.

15. The graph structure analysis method according to claim 12, further comprising
   outputting the extracted feature representation as an attribute to be used in the machine learning.

16. A non-transitory computer readable recording medium in which a program for causing a computer with a processor to analyze a graph structure is recorded, the program including instructions that, when executed by a processor, causes the processor to perform:
   selecting an analysis target range in the graph structure and a comparison target range to be compared with the analysis target range;
   extracting a feature representation from data related to the analysis target range and the comparison target range, for each of the ranges;
   displaying the extracted feature representation for each of the analysis target range and the comparison target range,
   wherein, in the extracting, clustering is performed on the data related to the analysis target range and the comparison target range to generate a plurality of clusters, and the feature representation is extracted from the generated clusters for each of the analysis target range and the comparison target range, and
   in the displaying, the plurality of clusters is displayed in addition to the extracted feature representation for each of the analysis target range and the comparison target range.

* * * * *